United States Patent
Meckel

(10) Patent No.: US 6,656,186 B2
(45) Date of Patent: Dec. 2, 2003

(54) BONE SAW BLADE AND A METHOD FOR MANUFACTURING A BONE SAW BLADE

(75) Inventor: Nathan K. Meckel, La Mesa, CA (US)

(73) Assignee: Molecular Metallurgy, Inc., El Cajon, CA (US)

( * ) Notice: Subject to any disclaimer, the term of this patent is extended or adjusted under 35 U.S.C. 154(b) by 6 days.

(21) Appl. No.: 10/128,211

(22) Filed: Apr. 22, 2002

(65) Prior Publication Data

US 2003/0199880 A1 Oct. 23, 2003

(51) Int. Cl.[7] ............................................... A61B 17/14
(52) U.S. Cl. ............................. 606/82; 606/178; 30/350
(58) Field of Search ......................... 606/79, 82, 176, 606/178; 30/350, 346.54

(56) References Cited

U.S. PATENT DOCUMENTS

| | | | |
|---|---|---|---|
| 4,617,930 A | * | 10/1986 | Saunders |
| 4,653,373 A | * | 3/1987 | Gerber |
| 5,306,285 A | | 4/1994 | Miller |
| 5,724,868 A | | 3/1998 | Knudsen |
| 6,076,264 A | * | 6/2000 | Meckel .................. 30/225 |
| 6,110,177 A | * | 8/2000 | Ebner et al. ............. 606/84 |
| 6,330,750 B1 | * | 12/2001 | Meckel .................. 30/350 |

* cited by examiner

*Primary Examiner*—Ralph A. Lewis
(74) *Attorney, Agent, or Firm*—Nydegger & Associates

(57) ABSTRACT

A bone saw blade includes a blade body having a cutting section, a hub section and a shank located between the cutting section and the hub section. The blade body is first formed having a substantially uniform Rockwell hardness between approximately $R_c$ 49 and $R_c$ 63 throughout. Next, a cathodic arc process is used to coat the cutting section with a hard, wear-resistant metal nitride coating. During the coating process, ion impingement on the surface of the cutting section creates heat that beneficially anneals the cutting section. Significant annealing of the shank and hub section is prevented during the coating process by stacking the blade bodies together with blade blanks that are formed without cutting sections. The heat generated during coating is insufficient to raise the temperature of the large mass above the annealing temperature of the blade material. The resultant blade has a high strength shank and hub section.

20 Claims, 4 Drawing Sheets

BONE SAW BLADE AND A METHOD FOR MANUFACTURING A BONE SAW BLADE

FIELD OF THE INVENTION

The present invention pertains generally to bone saw blades and methods for manufacturing bone saw blades. More particularly, the present invention pertains to bone saw blades having a hard, wear resistant coating on their cutting surface. The present invention is particularly, but not exclusively, useful for a bone saw blade having a ductile cutting section that is coated with a wear resistant coating and a hard, wear-resistant hub for attaching the blade to a power tool.

BACKGROUND OF THE INVENTION

It is often necessary to surgically resect a portion of a patient's bone. To perform this procedure, an opening or pathway to the bone is necessarily required to expose the bone. To minimize the size of this pathway, specially designed bone saw blades are generally used in the resection procedure. More specifically, a typical bone saw blade has a thin, flat, elongated shape with a cutting edge at one end. The thin, flat design minimizes the size of the required pathway and allows the blade to be held against a cutting guide during the cut to ensure an accurate, straight cut. The cutting edge is generally oriented along a direction that is orthogonal to the direction of blade elongation and contains a plurality of teeth. Thus, when the blade is inserted into the pathway, the cutting edge can be pressed against the surface of the bone that requires resection.

At the other end of the bone saw blade, the blade contains a hub section for attachment to a hand operated power tool. The power tool imparts a reciprocating motion to the blade causing the teeth of the blade to move back and forth along a cutting line that is co-linear with the cutting edge. During this process, the blade is subjected to several forces. The teeth and portions of the blade near the teeth often experience impact type forces as the oscillating teeth strike the hard bone. If the teeth are too hard and brittle, the impact forces can cause cracks in the teeth (or portions of the blade near the teeth) which will propagate and lead to a brittle fracture of the blade. In a worst case scenario, one or more of the teeth or very small particulates may break away from the blade, remain in the patient, and may result in "metalosis".

In addition to impact type forces, the surfaces of the teeth are also subjected to wear type forces that can cause material removal and galling of the teeth. These processes tend to cause an unwanted dulling of the teeth and cutting edge. On the other hand, unlike the forces exerted on the teeth at the cutting section, the thin shank of the blade (i.e. the portion of the blade between the cutting section and the hub section) is generally exposed to twisting and bending forces during a cut that tend to distort the shape of the blade. To minimize this distortion, the shank is preferably made of a relatively strong and tough material.

At the hub section of the blade, oscillation forces are transmitted from the power tool to the blade. It is to be appreciated that the surface of the hub section is subjected to wear type forces that can cause material removal and galling. Unfortunately, these processes tend to cause a loose, sloppy fit between the blade and the power tool, causing an inaccurate cut. Additionally, like the shank, the hub section is often exposed to twisting and bending forces during a cut that can distort the shape of the blade. Thus, the hub section of the blade is preferably made of a hard, strong material to prevent surface wear and minimize distortion.

Importantly, the strength, hardness, and ductility of many engineering materials can be selectively altered using heat treating, annealing, and cold working processes. Annealing is a thermal treatment that is often used to increase the ductility and toughness (at the expense of hardness) of steel (including stainless steels). Metallurgically, annealing involves subjecting a material to an elevated temperature to reduce dislocations, vacancies and other metastable conditions in the material. On the other hand, cold working a steel by processes such as drawing or rolling increases the dislocation density in the material, and thus, increases the strength and hardness (at the expense of ductility) of the material. Thus, a wide range of mechanical properties is obtainable for a given material through the selective use of cold working and annealing processes.

Heretofore, a typical procedure for manufacturing a bone saw blade has been to stamp the blade from a cold-rolled sheet of stainless steel having a hardness in excess of 42 on the Rockwell C scale ($R_c$ 42). Next, while the blade is still hard, the teeth are machined. Unfortunately, in this cold rolled condition, the teeth lack ductility and toughness. To prevent brittle fracture in or near the teeth during subsequent use, the entire blade is typically annealed resulting in a blade having a substantially uniform hardness of between, for example, approximately $R_c$ 49 to $R_c$ 51. Although this annealing treatment imparts some ductility to the teeth, the surfaces of the teeth and hub section are also softened leading to excessive wear. Another drawback that occurs when the entire blade is annealed is that the strength of the blade shank is significantly reduced increasing the tendency of the blade to distort during use.

In light of the above, it is an object of the present invention to provide a bone saw blade having a strong hub section together with a cutting section that is coated with a hard wear resistant material. It is another object of the present invention to provide methods for manufacturing a stainless steel bone saw. blade having a cutting section with a hardness of between approximately $R_c$ 42 and $R_c$ 58 and a shank and hub section having a hardness between approximately $R_c$ 49 and $R_c$ 63. It is yet another object of the present invention to provide a method for manufacturing a stainless steel bone saw blade having a fracture-resistant and deformation-resistant cutting section together with a strong, wear resistant shank and hub section. Yet another object of the present invention is to provide a stainless steel bone saw blade which is safe to use, does not dull easily, and is comparatively cost effective.

SUMMARY OF THE PREFERRED EMBODIMENTS

The present invention is directed to a bone saw blade and a method for manufacturing a bone saw blade. In overview, the bone saw blade includes a blade body that is partially coated with a hard wear-resistant coating. In terms of shape, the blade body is formed with a first substantially flat surface and an opposed second substantially flat surface. Between the flat surfaces, the blade body can be characterized as being relatively thin in section. Accordingly, a blade thickness, t, can be defined as the thickness between the flat surfaces. In addition, the thin blade body is elongated defining a longitudinal axis in the direction of elongation. For the present invention, the blade body can be further characterized as having three distinct sections. Specifically, the blade body includes a cutting section at one end of the blade body, a hub section at the opposite end of the blade body and a shank located between the cutting section and the hub section.

Within the hub section, the blade body is preferably formed with one or more recesses, holes or slots for engagement with a hand operated power tool. At the other end of the blade body, the cutting section includes a plurality of teeth that define a cutting edge. Preferably, the cutting edge extends in a direction that is orthogonal to the longitudinal axis and lies within the plane of the thin bone saw blade. The cutting section further includes approximately 3–7 mm of blade that is positioned between the teeth and the blade body. As described further below, a hard, wear resistant coating is applied to the surface of the cutting section.

For the present invention, the blade body is preferably fabricated from a stainless steel material, but can be manufactured using titanium or zirconium alloys. Importantly, the manufacturing method used to prepare the blade is controlled to produce specific mechanical properties within the different blade body sections. In greater detail, the blade is manufactured having a cutting section that is relatively ductile with a Rockwell hardness between approximately $R_c$ 42 and $R_c$ 58. This ductility allows the cutting section including the teeth to accommodate impact type forces without fracture. On the other hand, the shank and hub section are manufactured to be relatively strong and hard having a Rockwell hardness between approximately $R_c$ 49 and $R_c$ 63. The strong shank prevents unwanted distortion of the blade during a cut and the hard hub section inhibits wear and prevents the attachment between the blade and the power tool from becoming loose and sloppy.

In accordance with the methods of the present invention, the blade body is first formed having a substantially uniform Rockwell hardness between approximately $R_c$ 42 and $R_c$ 63 throughout. Next, the surface of the cutting section is coated with a hard, wear resistant coating. Preferably, the coating is a metal nitride coating that is deposited on the cutting section using a cathodic arc process. During the coating process, ion impingement on the surface of the cutting section creates heat that anneals the cutting section. As envisioned for the present invention, this annealing reduces the hardness of the cutting section from a hardness in a range between $R_c$ 49 and $R_c$ 63 to a hardness in a range between approximately $R_c$ 42 and $R_c$ 58, dependent upon the materials being used.

Importantly, in accordance with the methods of the present invention, significant annealing of the shank and hub section is prevented during the coating process. In particular, during the coating process, a plurality of blade bodies are stacked on a fixture. Blade blanks are positioned between adjacent blade bodies within the stack. Each blank has substantially the same shape as the blade bodies with each blank being slightly larger that the blade bodies. The blanks also differ from the blades in that the blanks do not contain a cutting section. Thus, the blanks are somewhat shorter than the blades. With this cooperation of structure, the shank and hub section of each blade are sandwiched between a pair of blanks in the stack. On the other hand, the cutting section of each blade body is left exposed and a gap (having a thickness equal to the thickness, d, of each blank) is established between adjacent cutting sections.

During coating of the cutting sections, the blade bodies and blanks combine together to present a large mass that will absorb the heat that is generated due to ion impingement of the cutting sections. By design, the mass (blades and blanks) is large enough to prevent the heat from raising the mass above the temperature that is required to anneal the material of the blade body. The exposed cutting section, however, is annealed by the heat to a ductile condition. The as-formed strength of the shank and hub sections, however, is maintained through the coating process.

BRIEF DESCRIPTION OF THE DRAWINGS

The novel features of this invention, as well as the invention itself, both as to its structure and its operation, will be best understood from the accompanying drawings, taken in conjunction with the accompanying description, in which similar reference characters refer to similar parts, and in which.

DESCRIPTION OF THE PREFERRED EMBODIMENT

Figure 1:
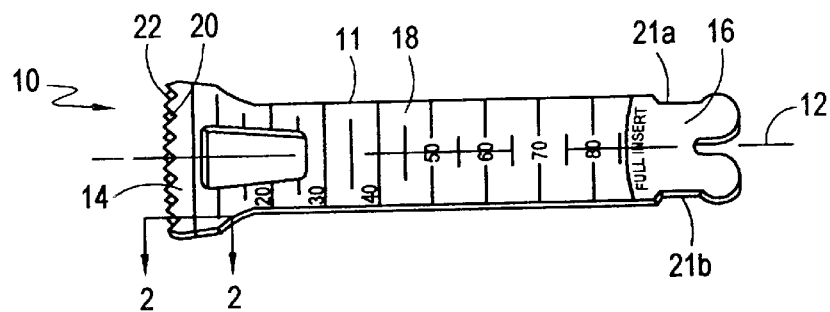
FIG. 1 is a perspective view of a bone saw blade in accordance with the present invention.

Referring to FIG. 1, a bone saw blade in accordance with the present invention is shown and generally designated 10. As shown in FIG. 1, the blade 10 has a blade body 11 that is substantially flat and is preferably relatively thin in section. Additionally, the thin blade body 11 is elongated defining a longitudinal axis 12 in the direction of elongation. For the present invention, as shown in FIG. 1, the blade body 11 can be characterized as having three distinct sections; a cutting section 14, a hub section 16 and a shank 18 located between the cutting section 14 and the hub section 16. As detailed further below (and see FIG. 2A), a coating 19 is deposited on the cutting section 14 of the blade body 11.

Referring still to FIG. 1, it can be seen that the hub section 16 is formed with recesses 21a, b for engagement with a hand operated power tool (not shown). It is to be appreciated by those skilled in the pertinent art that other types of hub designs to include various slots, holes or recesses can be used in the blade 10 of the present invention. It is to be further appreciated that the power tool is configured to oscillate the blade 10 in operation, and that a tight fit between the hub section 16 and the power tool is required to provide an accurate cut.

With continued reference to FIG. 1, it can be seen that the cutting section 14 of the blade 10 includes a plurality of aligned or off-set teeth 20 that define a cutting edge 22. As shown, the cutting edge 22 preferably extends in a direction that is orthogonal to the longitudinal axis 12 and lies within the plane of the thin bone saw blade 10. In addition to the teeth 20, the cutting section 14 further includes a portion of the blade 10 located between the teeth 20 and the shank 18. In a preferred embodiment of the present invention, the cutting section 14 includes the teeth 20 and a portion of the blade body 11 that extends inward towards the shank 18 approximately 3–7 mm along the axis 12.

Figure 2A:
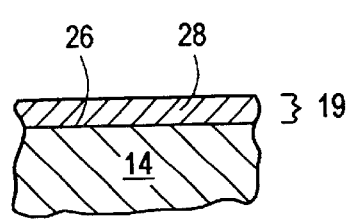
FIG. 2A is an enlarged, sectional view of a portion of the cutting section of the blade as seen along line 2—2 in FIG. 1 showing a coating having a single layer.

With cross-reference now to FIGS. 1 and 2A, it can be seen that a coating 19 is deposited on the surface 26 of the cutting section 14 (i.e. a coating 19 is deposited on the surface of the teeth 20 and the portion of the blade body 11 described above that is located between the teeth 20 and the shank 18). As detailed further below, the coating 19 is preferably deposited using a cathodic arc source, but could also be deposited using thermal evaporation or magnatron sputtering. As shown, the coating 19 includes a layer 28 which is preferably a metal nitride material. Examples of metal nitrides that can be used in the present invention include nitrides of vanadium, chromium, zirconium, titanium, niobium, molybdenum, hafnium, tantalum and tungsten. In more preferred embodiments of the present invention, metal nitrides of chromium, zirconium, titanium, or hafnium are used. Carbon can be added to form carbonitrides of the same metals.

Figure 2B:
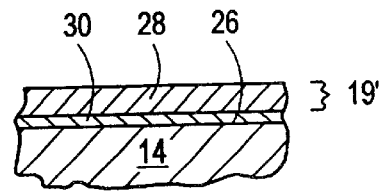
FIG. 2B is an enlarged, sectional view as in FIG. 2A showing an alternate embodiment of the present invention in which a coating having two layers is used.

As shown in FIG. 2B, in an alternate embodiment of the present invention, a multi-layer coating 19' can be deposited on the surface 26 of the cutting section 14. As further shown, the multi-layer coating 19' can include a metal layer 30 and a layer 28 which is preferably a metal nitride material as described above. Examples of metals that can be used in the metal layer 30 for the present invention include vanadium, chromium, zirconium, titanium, niobium, molybdenum, hafnium, tantalum and tungsten. In accordance with the present invention, the metal layer 30 is used to promote adhesion between the metal nitride layer 28 and the surface 26 of the cutting section 14.

Figure 2C:
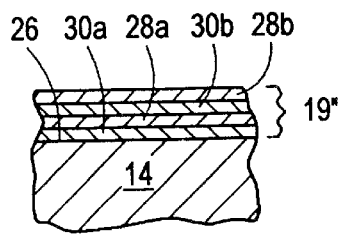
FIG. 2C is an enlarged, sectional view as in FIG. 2A showing an alternate embodiment of the present invention in which a coating having four layers is used.

Referring now to FIG. 2C, an alternate embodiment of the present invention is shown wherein the coating 19" includes alternating layers of metal 30a, b (as described above) and metal nitride 28a, b (as described above) on the surface 26 of the cutting section 14. Although four layers are shown in FIG. 2C, it is to be appreciated that a coating 19" having any number of metal layers 30a, b and any number of layers of metal nitride 28a, b can be used in accordance with the present invention.

Figure 2D:
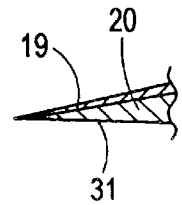
FIG. 2D is an enlarged, not to scale, sectional view as seen along line 2—2 in FIG. 1 showing a tooth that has been coated and then had a portion of the coating removed to provide a tooth that is self-sharpening.

If desired, the coating 19 can be removed from one surface 31 as shown in FIG. 2D. Functionally, removal of the coating 19 from one surface 31 of each tooth 20 produces a blade 10 that is self-sharpening. In one embodiment of the present invention, coating removal is accomplished using a grinding process.

Referring back to FIG. 1, it can be seen that the blade body 11, which includes the cutting section 14, shank 18 and hub section 16 is preferably of one piece construction. For the present invention, the blade body 11 is preferably made of a steel material. In more preferable embodiments, the blade body 11 is made of a stainless such as 716, 440, 420, 410, 301, 302, 316 and others, to include non-stainless steel materials such as titanium and zirconium alloys. These are preferred materials due to their corrosion resistance and biocompatibility. Importantly, the manufacturing method used to prepare the blade 10 is designed to produce specific mechanical properties within the different sections of the blade body 11 (i.e. the cutting section 14, shank 18 and hub section 16). In greater detail, the blade 10 is manufactured having a cutting section 14 that is relatively ductile with a Rockwell hardness between approximately $R_c$ 42 and $R_c$ 58. On the other hand, the shank 18 and hub section 16 are manufactured to be relatively strong and hard having a Rockwell hardness between approximately $R_c$ 49 and $R_c$ 63.

In accordance with the methods of the present invention, the body 11 of the blade 10 is first formed having a substantially uniform Rockwell hardness between approximately $R_c$ 49 and $R_c$ 63 throughout. For example, the body 11 can be stamped out of a sheet of material having a uniform hardness, or the blade body 11 can be forged using techniques that are well known in the pertinent art. Once the general shape of the body 11 has been established, features such as the teeth 20 can be machined.

With the body 11 having a uniform hardness between approximately $R_c$ 49 and $R_c$ 63, the next step in the methods of the present invention is to coat the cutting section 14 with a hard, wear resistant coating 19 (see FIG. 2A). As described further below, a cathodic arc process is preferably used to deposit the coating 19. In this process, heat is created due to ion impingement that anneals the cutting section 14. Importantly, in accordance with the methods of the present invention, significant annealing of the shank 18 and hub section 16 is prevented during the coating process. More specifically, fixturing is used to control the temperature of the shank 18 and hub section 16 during the coating of the cutting section 14 to prevent significant annealing of the shank 18 and hub section 16.

Figure 3:
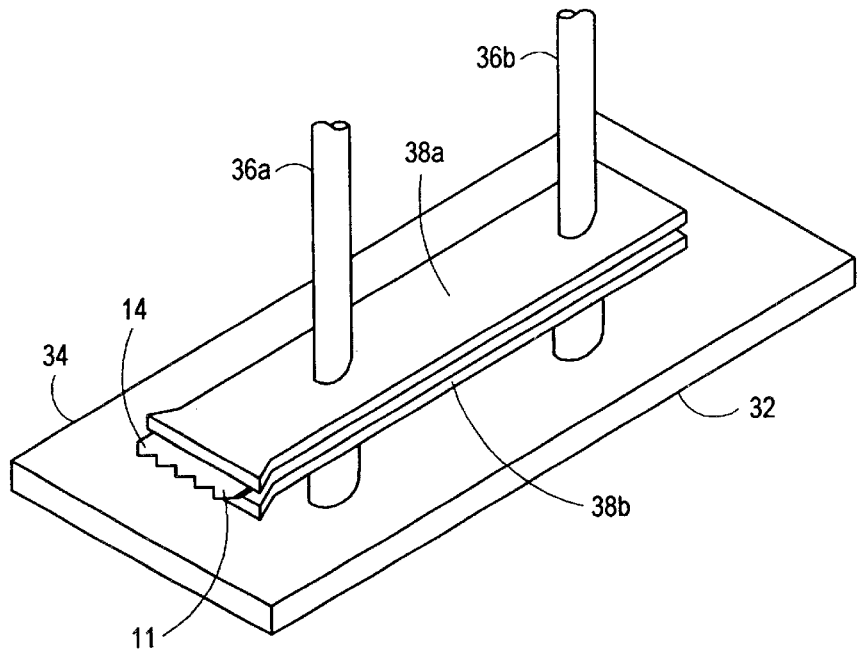
FIG. 3 is a perspective view of a fixture supporting the blade shown in FIG. 1 sandwiched between two blade blanks.
Figure 4:
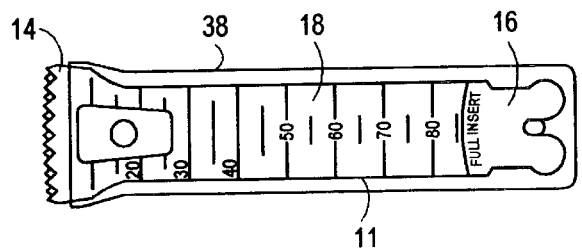
FIG. 4 is a plan view of the blade shown in FIG. 1 positioned on a blade blank.

Referring now to FIG. 3, a fixture 32 for use during the coating step of the present invention is shown. As shown, the fixture 32 has a base 34 and rods 36a, b that extend from the base 34. As further shown, a plurality of blade blanks 38a, b are disposed on the rods 36a, b. Referring to FIG. 4, it can be seen that each blank 38 has substantially the same shape as the blade body 11 with the exception that the blank 38 is somewhat wider than the blade body 11 and the blank 38 does not contain a cutting section 14. Thus, each blank 38 is somewhat shorter than the blade body 11. Cross referencing FIGS. 3 and 4, is can be seen that the shank 18 and hub section 16 of each blade body 11 is sandwiched between a pair of blanks 38a, b. With the shank 18 and hub section 16 disposed between blanks 38a, b, the cutting section 14 of each blade body 11 is left exposed to receive coating 19 (shown in FIG. 2A).

Figure 5:
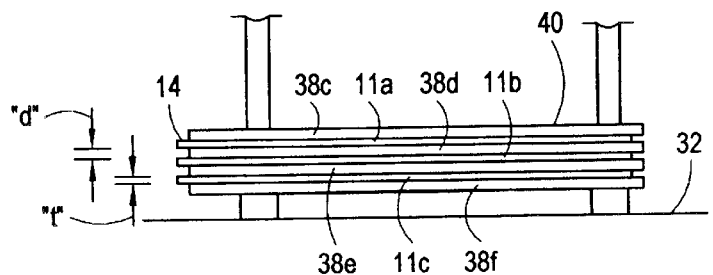
FIG. 5 is an elevation view of a stack of blades and blanks positioned on a coating fixture.

In a preferred embodiment of the present invention as shown in FIG. 5, a stack 40 having a plurality of blade bodies, such as blade bodies 11a–c, and a plurality of blanks, such as 38c–f, is disposed on the fixture 32 for use in the coating step. For the present invention, as few as one and as many as a hundred or more blade bodies 11 can be disposed in each stack 40. As shown in FIG. 5, each blade body 11 has a thickness, t, and each blank 38 has a thickness, d. Thus, adjacent blade bodies 11 are separated within the stack 40 by a gap having a thickness equal to the thickness, d, of each blank 38.

Functionally, the blade bodies 11 and blanks 38 in the stack 40 combine to create a relatively large mass. Due to this relatively large mass, the heat generated due to ion impingement during coating of the cutting sections 14 is insufficient to raise the shank 18 and hub section 16 of each blade body 11 above the annealing temperature of the blade material (e.g. stainless steel). Thus, only the exposed cutting section 14 is annealed to a ductile condition during coating. The coated blade 10 that results has a cutting section 14 that is relatively ductile with a Rockwell hardness between approximately $R_c$ 42 and $R_c$ 58, and a shank 18 and hub section 16 that are relatively strong and hard having a Rockwell hardness between approximately $R_c$ 49 and $R_c$ 63.

Several factors are considered in selecting the thickness, d, of the blade blanks 38. A first consideration, as indicated above, is the mass required to prevent annealing of the shank 18 and hub section 16 of each blade body 11. Holding other factors constant, it is to be appreciated that increasing the thickness, d, of the blanks 38 effectively increases the mass of the stack 40. Another consideration is the amount of ion impingement that occurs in the cutting section 14. For progressively thicker blade bodies 11, increased levels of ion impingement is required to anneal the thicker cutting section 14. These increased levels of ion impingement can be obtained by increasing the spacing between adjacent cutting sections 14 in the stack 40, which can be achieved using thicker blade blanks 38. Thus, the thickness, t, of the blade body 11 drives the thickness, d, of the blade blanks 38 required to both ensure that the cutting section 14 is properly annealed and preventing the shank 18 and hub section 16 of each blade body 11 from annealing.

Figure 6:
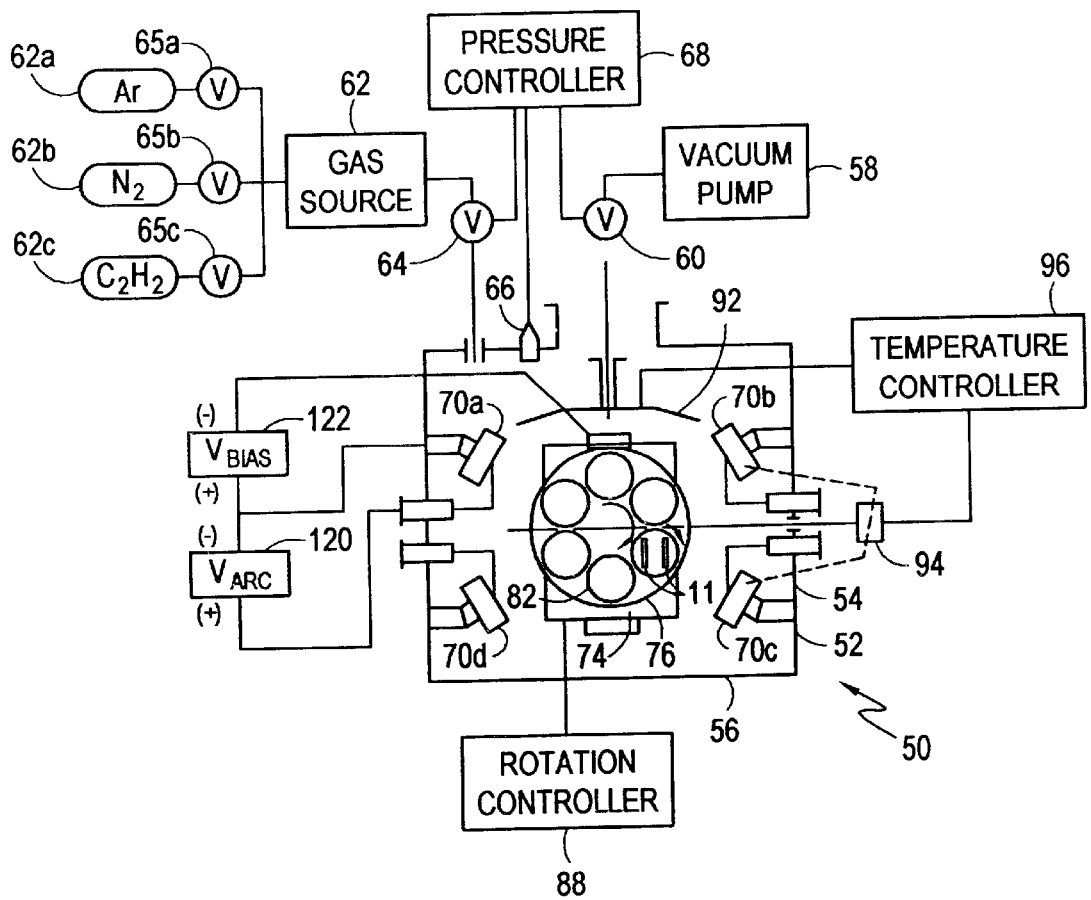
FIG. 6 is a schematic plan view and control diagram of a deposition apparatus for use in the invention.
Figure 7:
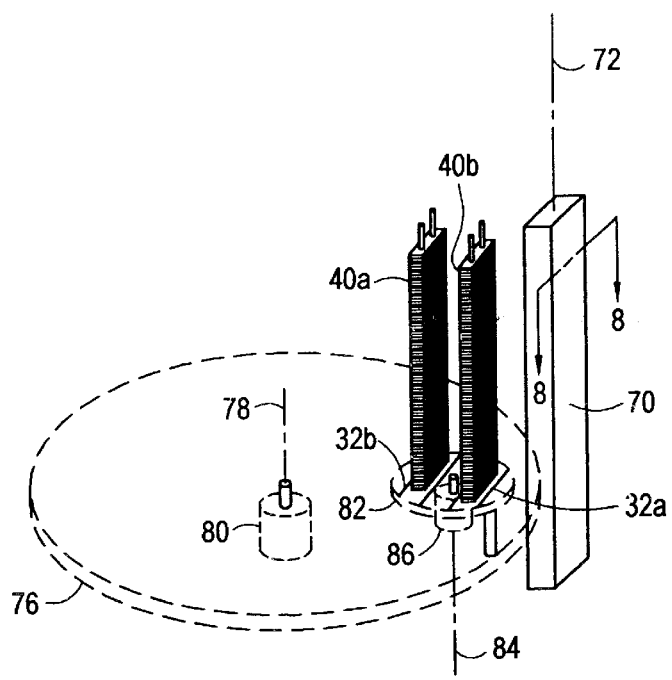
FIG. 7 is a schematic perspective view of a detail of the deposition apparatus of FIG. 6.

FIGS. 6 and 7 depict a preferred deposition apparatus 50 for coating the blade bodies 11, although other operable deposition apparatus may be used. The deposition apparatus 50 includes a chamber 52 having a body 54 and a door 56 that may be opened for access to the interior of the chamber 52 and which is hermetically sealed to the body 54 when the chamber 52 is in operation. The interior of the chamber 52 is controllably evacuated by a vacuum pump 58 pumping through a gate valve 60. The vacuum pump 58 includes a mechanical pump and a diffusion pump operating together in the usual manner. The interior of the chamber 52 may be controllably backfilled to a partial pressure of a selected gas from a gas source 62 through a backfill valve 64. The gas source 62 typically includes several separately operable gas sources. The gas source 62 usually includes a source 62a of an inert gas such as argon, a source 62b of nitrogen gas, and a source 62c of a carbon-containing gas such as acetylene, each providing gas selectively and independently through a respective selector valve 65a, 65b, or 65c. Other types of gas can also be provided as desired.

The pressure within the chamber 52 is monitored by a vacuum gage 66, whose output signal is provided to a pressure controller 68. The pressure controller 68 controls the settings of the gate valve 60 and the backfill valve 64 (and, optionally, the selector valves 65), achieving a balance of pumping and backfill gas flow that produces a desired pressure in the chamber 52 and thence pressure reading in the vacuum gage 66. Thus, the gaseous backfilled atmosphere within the chamber 52 is preferably a flowing or dynamic atmosphere.

At least two, and preferably four as shown, linear deposition sources 70 are mounted within the interior of the chamber 52 in a circumferentially spaced-apart manner. In FIG. 6, the four deposition sources are identified as distinct sources 70a, 70b, 70c, and 70d, as they will be addressed individually in the subsequent discussion. The four deposition sources 70 are generally rectangular bodies having a greatest rectilinear dimension elongated parallel to a source axis 72. This type of deposition source is distinct from either a stationary point source or a point source that moves along the length of the substrate during deposition procedures.

A substrate support 74 is positioned in the chamber 52. The substrate support 74 produces a compound rotational movement of a substrate mounted thereon. The preferred substrate support 74 includes a rotational carriage 76 that rotates about a rotational axis 78, driven by a rotational drive motor 80 below the rotational carriage 76. Mounted on the rotational carriage 76 are at least one and preferably six, as shown, planetary carriages 82. The planetary carriages 82 are rotationally driven about a rotational axis 84 by a planetary drive motor 86 below the planetary carriages 82. The speeds of the rotational drive motor 80 and the planetary drive motor 86 are controlled by a rotation controller 88. The rotation controller 88 preferably rotates the rotational carriage 76 at a rate of about 1 revolution per minute (rpm).

Continuing with FIGS. 6 and 7, for deposition processing one or more stacks, such as stacks 40a, b having blade bodies 11 and blanks 38 (see FIG. 5) are disposed on fixtures 32a, b as described above and the fixtures 32a, b are mounted on the planetary carriage 82, as shown. For commercial operations, two stacks 40 having blade bodies 11 are typically mounted on each planetary carriage 82 in the manner described, as illustrated for one of the planetary carriages 82 in FIG. 7.

The temperature in the chamber 52 during deposition is controlled using a heater 92 that extends parallel to the deposition sources 70 on one side of the interior of the chamber 52. The heater 92 is preferably a radiant heater operating with electrical resistance elements. The temperature of the heating array is monitored by a temperature sensor 94 such as an infrared sensor that views the interior of the chamber 52. The temperature measured by the sensor 94 is provided to a temperature control circuit 96 that provides the power output to the heater 92. Acting in this feedback manner, the temperature controller 96 allows the temperature of the heating array to be set. In the preferred processing, the heating array is heated to a temperature of from about 400° F. to about 1650° F.

Figure 8:
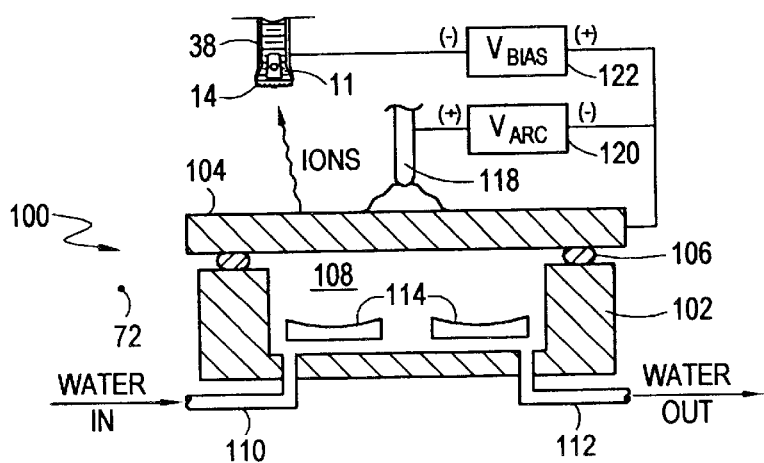
FIG. 8 is a schematic sectional view of a preferred cathodic arc source, taken along lines 8—8 of FIG. 7.

FIG. 8 illustrates a cathodic arc source 100 used in the preferred form of the deposition source 70. The cathodic arc source 100 includes a channel-shaped body 102 and a deposition target 104. The deposition target 104 is in the form of a plate that is hermetically sealed to the body 102 using an O-ring 106, forming a water-tight and gas-tight hollow interior 108. The interior 108 is cooled with cooling water flowing through a water inlet 110 and a water outlet 112. Two spirally shaped (only sections of the spirals are seen in FIG. 8) permanent magnets 114 extend parallel to the source axis 72. Positioned above the deposition target 104 exterior to the body 102 is a striker electrode 118. A voltage $V_{ARC}$ is applied between the striker electrode 118 and the deposition target 104 by an arc source power supply 120. $V_{ARC}$ is preferably from about 10 to about 50 volts.

The metallic material that initially forms the deposition target 104 is deposited onto the cutting section 14 of the blade body 11, together with, if desired, gas atoms producing gaseous species from the atmosphere of the chamber 52. In the preferred embodiment, the deposition target 104 is made of zirconium (Zr) or titanium (Ti). Other metallic species operable as the deposition target material include metals found in Groups IV–VI of the Periodic Table, including but not limited to vanadium, chromium, niobium, molybdenum, hafnium, tantalum, and tungsten. Other metals such as aluminum may be used. The deposition target 104 may also be made of alloys or intermetallic compounds such as, for example, Ti—6Al—4V, $Ti_3Al$, TiAl, or AlTi.

To accomplish the deposition, an arc is struck between the striker electrode 118 and the deposition target 104, locally heating the deposition target 104 and causing zirconium or titanium atoms and/or ions to be ejected from the deposition target 104. (The deposition target 104 is therefore gradually thinned as the deposition proceeds.) The striking point of the arc on the deposition target 104 moves in a racetrack course along the length of the deposition target 104. A negative bias voltage $V_{BIAS}$ is applied between the deposition target 104 and the blade body 11 by a bias power supply 122, so that any positively charged ions are accelerated toward the substrate.

$V_{BIAS}$ is preferably from about −30 to about −600 volts. The value selected for $V_{BIAS}$ determines the energy of ionic impact against the surface of the substrates, a phenomenon termed ion peening. In a typical case, $V_{BIAS}$ is initially selected to be a relatively large negative voltage to achieve good adherence of the first metallic layer to the substrate. $V_{BIAS}$ is subsequently reduced (made less negative) when overlying hard layers are deposited, to achieve a uniform, fine microstructure in the layers. The values of $V_{BIAS}$ are desirably maintained as low as possible consistent with obtaining an adherent coating 19. $V_{BIAS}$ is more positive than −600 volts, and most preferably more positive than −400 volts. If $V_{BIAS}$ is too negative, corona effects and backsputtering may occur at some regions of the cutting section 14 of the blade body 11. Thus, while higher $V_{BIAS}$ voltages may be used in some instances, generally it is preferred that $V_{BIAS}$ be more positive than −600 volts. The cathodic arc source 100 is preferred, but other types of sources, such as sputtering sources, may also be used.

The cooperative selection of the material of the deposition target 104 and the gases introduced into the deposition chamber 52 from the gas source 62 allows a variety of coatings 19 to be deposited onto the cutting section 14 of the blade body 11, within the constraints discussed previously. In all cases, the total thickness of the coating 19 is preferably from about 1 to about 10 micrometers. If the coating thickness is less than about 1 micrometer, the physical properties of the coating 19 are insufficient to produce the desired results. If the coating thickness is more than about 10 micrometers, the coating 19 has a high internal stress that leads to a tendency for the coating 19 to crack and spall away from the member substrate during deposition or during service.

These general principles are applied in preparing the coatings 19 of interest, as described previously in relation to FIGS. 2A–C. The coating 19 of FIG. 2A includes a layer 28 of metal nitride, which is deposited by backfilling the deposition chamber 52 with a small partial pressure of about 5 microns of flowing nitrogen (flowing at a rate of about 150–500 seen in the inventors' apparatus), and then depositing a metal such as titanium or zirconium from the deposition target 104 with $V_{BIAS}$ about −50 volts. The metal combines with the nitrogen to produce the metal nitride coating 19 in the layer 28.

The coating 19' of FIG. 2B includes a metal layer 30, such as metallic zirconium or metallic titanium, contacting the surface 26 of the cutting section 14. The metal layer 30 aids in adhering the overlying layer(s) to the surface of the substrate. The metal layer 30 is preferably quite thin, on the order of from about 100 Angstroms to about 1000 Angstroms thick. The metal layer 30 is deposited by backfilling the deposition chamber 52 with a small partial pressure of about 5 microns of an inert gas, such as flowing argon (flowing at a rate of about 200–450 standard cubic centimeters per minute (sccm) in the apparatus used by the inventors), and then depositing metal, such as zirconium or titanium, from the deposition target 104 with $V_{BIAS}$ about −400 volts. Because the argon does not chemically react with the metal, a metallic layer 30 is deposited. As shown in FIG. 2B, a layer 28, which is a metal nitride, overlies the metal layer 30. The layer 28 is deposited by backfilling the deposition chamber 52 with a small partial pressure of about 5 microns of flowing nitrogen (flowing at a rate of about 150–500 seen in the inventors' apparatus), and then depositing metal, such as zirconium or titanium, from the deposition target 104 with $V_{BIAS}$ about −50 volts. The metal combines with the nitrogen to produce the metal nitride coating 19 in the layer 28. The layer 28 is preferably of a thickness such that the total thickness of the coating 19 is from about 1 to about 10 micrometers.

This pattern may be continued, depositing a third layer comprising metal then a fourth layer comprising metal nitride as shown in FIG. 2C. The topmost layer is, in all cases, metal nitride. In this case, the thicknesses of the individual layers are selected so that the total thickness of the coating 19 is from about 1 to about 10 micrometers. Various other compositions may be substituted for one or more of these layers, as well.

When a single metallic species is to be deposited into the coating 19, as in the embodiments of FIGS. 2A–2C, all of the deposition sources 70a, 70b, 70c, and 70d utilize deposition targets 104 made of that species. When two metallic species such as titanium and aluminum are to be deposited, some of the deposition sources 70 utilize titanium and/or aluminum deposition targets 104, and some of the deposition sources 70 may utilize alloy deposition targets 104 such as TiAl deposition targets. For example, the deposition sources 70a and 70c might be made with titanium deposition targets 104, and the deposition sources 70b and 70d might be made with titanium-aluminum deposition targets 104. All of the deposition sources 70 would be operated during deposition of the titanium layer (with inert gas in the chamber 52), and only the deposition sources 70 with TiAl targets would be used to deposit a (TiAl)N layer (with nitrogen gas in the chamber 52).

While the particular bone saw blade as herein shown and disclosed in detail is fully capable of obtaining the objects and providing the advantages herein before stated, it is to be understood that it is merely illustrative of the presently preferred embodiments of the invention and that no limitations are intended to the details of construction or design herein shown other than as described in the appended claims.

What is claimed is:

1. A bone saw blade for use with a power tool which comprises:

an elongated shank having a first end and a second end, said shank having a first hardness;

a hub extending from the first end of said shank for engagement with the power tool, said hub having substantially the same first hardness;

a cutting section formed with a cutting edge extending from the second end of said shank, said cutting section having a second hardness; and a coating on said cutting section with said coating having a third hardness wherein the third hardness is greater than the first hardness, and the first hardness is greater than the second hardness.

2. A bone saw blade as recited in claim 1 wherein said coating comprises a layer of metal nitride.

3. A bone saw blade as recited in claim 2 wherein said metal nitride is a nitride of a metal selected from the group of metals consisting of Titanium, Zirconium, Hafnium and Chromium.

4. A bone saw blade as recited in claim 1 wherein said coating comprises at least one layer of metal and at least one layer of metal nitride.

5. A bone saw blade as recited in claim 1 wherein said coating comprises at least one layer of titanium metal and at least one layer of titanium nitride.

6. A bone saw blade as recited in claim 1 wherein said shank, said hub and said cutting element are made of steel and said first hardness is between approximately $R_c$ 49 and approximately $R_c$ 63 and said second hardness is between approximately $R_c$ 42 and approximately $R_c$ 58.

7. A bone saw blade as recited in claim 1 wherein said steel is a stainless steel.

8. A method for manufacturing a bone saw blade, said method comprising the steps of:

provinding a stainless steel blade body, said blade body having a substantially uniform hardness, said hardness being between approximately $R_c$ 49 and approximately $R_c$ 63, said blade body formed with a hub and a cutting section having a surface; and impinging said surface of said cutting section with ions to anneal said cutting section and deposit a coating on said surface while maintaining said hub at a hardness between approximately $R_c$ 49 and approximately $R_c$ 63 during said impinging step.

9. A method as recited in claim 8 wherein said cutting section is formed with a plurality of teeth, and wherein said method further comprises the step of removing said coating from a portion of at least one said tooth to produce a bone saw blade that is self-sharpening.

10. A method as recited in claim 9 wherein the step of removing said coating from a portion of at least one said tooth is accomplished by grinding.

11. A method as recited in claim 8 wherein said maintaining step is accomplished by disposing said hub between a pair of blanks.

12. A method as recited in claim 8 wherein said impinging step anneals said cutting section to a hardness between approximately $R_c$ 42 and approximately $R_c$ 58.

13. A method as recited in claim 8 wherein said coating comprises a layer of a metal nitride.

14. A method as recited in claim 8 wherein said metal nitride is a nitride of a metal selected from the group of metals consisting of Titanium, Zirconium, Hafnium and Chromium.

15. A method as recited in claim 8 wherein said coating comprises at least one layer of a metal and at least one layer of a metal nitride.

16. A method as recited in claim 15 wherein said coating comprises at least one layer of titanium metal and at least one layer of titanium nitride.

17. A method as recited in claim 8 wherein said coating comprises a chemical combination of a first metal selected from the group consisting of vanadium, chromium, zirconium, titanium, niobium, molybdenum, hafnium, tantalum, and tungsten, and combinations thereof, and a nonmetal reactive with the first metal to produce a coating material, the nonmetal being selected from the group consisting of nitrogen and carbon, and combinations thereof, wherein the step of impinging includes the steps of:

providing a deposition apparatus comprising:
at least two linear deposition sources, each of the deposition sources lying parallel to a source axis and each of the deposition, sources being a source of the first metal;
a source of the nonmetal; and
a fixture adapted for rotational movement about the source axis;
mounting the blade in the fixture, rotating the substrate support about the source axis; and
operating the deposition sources to deposit the respective coating material onto said surface of said cutting section, the steps of rotating, and operating to occur simultaneously.

18. A method as recited in claim 8 wherein each said deposition source is a cathodic arc source.

19. A bone saw blade for use with a power tool, said bone saw blade comprising:

a first section formed with a hub for engagement with said power tool, said first section being made of a steel and having a hardness between approximately $R_c$ 49 and approximately $R_c$ 63;

a second section formed with a surface and having at least one sharpened edge for cutting, said second section being made of a steel and having a hardness between approximately $R_c$ 42 and approximately $R_c$ 58; and a coating overlaying said second section, said coating comprising at least one layer of a metal nitride material.

20. A bone saw blade as recited in claim 19 wherein said metal nitride is a nitride of a metal selected from the group of metals consisting of titanium, zirconium, hafnium and chromium.

* * * * *